United States Patent [19]

Freedman

[11] 4,117,122
[45] Sep. 26, 1978

[54] 11-AMINOALKYLMORPHANTHRIDIN-11-OLS

[75] Inventor: Jules Freedman, Cincinnati, Ohio

[73] Assignee: Richardson-Merrell Inc., Wilton, Conn.

[21] Appl. No.: 730,310

[22] Filed: Oct. 7, 1976

Related U.S. Application Data

[63] Continuation-in-part of Ser. No. 526,722, Nov. 25, 1974, abandoned.

[51] Int. Cl.$^2$ .................. A61K 31/635; C07D 223/00
[52] U.S. Cl. ............................... 424/244; 260/239 D
[58] Field of Search ................... 260/239 D; 424/244

[56] References Cited

U.S. PATENT DOCUMENTS

| 3,267,094 | 8/1966 | Drukker et al. | 260/239 D |
| 3,381,000 | 4/1968 | Drukker et al. | 260/239 |
| 3,692,906 | 9/1972 | Dage | 424/244 |
| 3,894,001 | 7/1975 | Drukker | 260/268 TR |

FOREIGN PATENT DOCUMENTS 1,470,003 10/1969 Fed. Rep. of Germany ...... 260/239 D

OTHER PUBLICATIONS

Drukker et al., J. Het. Chem. 2, 276–282 (1965).
Lakeside Labs, Chem. Abs. 62, 014642e (1964).
Drukker et al., Chem. Abs. 63, 14832a (1965).
Drukker et al., Chem. Abs. 63, 18056a (1965).

Primary Examiner—Donald G. Daus
Assistant Examiner—Mark L. Berch
Attorney, Agent, or Firm—George W. Rauchfuss, Jr.; Eugene O. Retter

[57] ABSTRACT

The compounds are 11-aminoalkylmorphanthridin-11-ols which are useful as antidepressant agents. The compounds disclosed are 11-(3-dimethylaminopropyl)morphanthridin-11-ol and 2-chloro-11-(3-dimethylaminopropyl)-5,6-dihydromorphanthridin-11-ol.

4 Claims, No Drawings

11-AMINOALKYLMORPHANTHRIDIN-11-OLS

RELATED APPLICATION

This application is a continuation-in-part of earlier copending application Ser. No. 526,722, filed Nov. 25, 1974, now abandoned

BACKGROUND OF THE INVENTION

Related compounds are disclosed in U.S. Pat. No. 3,381,000 and 3,153,652.

DESCRIPTION OF THE INVENTION

The compounds of the present invention may be represented by the following formula:

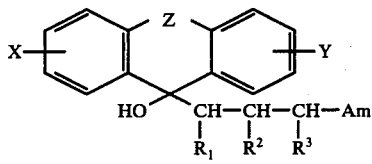

in which Z is

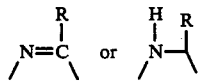

and R is hydrogen, $R_1$, $R_2$ and $R_3$ are hydrogen, X and Y are members of the group consisting of hydrogen and chloro with the proviso that when Z is

X and Y are both hydrogen and when Z is

X is hydrogen and Y is chloro at the 2-position, and Am is

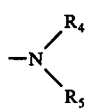

in which $R_4$ and $R_5$ are methyl.

The compounds of the present invention may be conveniently prepared from the corresponding 5,6-dihydromorphanthrin-11-ones which may be represented by the following formula:

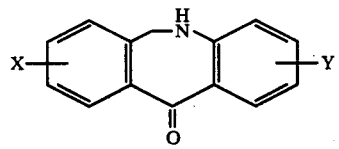

in which X and Y are as previously defined. These compounds are known compounds and may be prepared from the corresponding 6-chloromorphanthridones by hydrogenation.

Representative of the compounds that may be employed as starting materials are:

5,6-dihydromorphanthrin-11-one and
2-chloro-5,6-dihydromorphanthrin-11-one.

In the practice of the invention compounds are prepared by reacting a selected 5,6-dihydromorphanthrin-11-one with a disubstituted aminoalkyl metal halide under conditions generally used for reacting a Grignard reagent with a ketone to form a tertiary alcohol. The reactants are advisably combined in an anhydrous solvent such as ethyl ether, tetrahydrofuran or ethyl ether in combination with benzene. After the reactants have been combined, the mixture can, if desired, be heated at reflux to promote the reaction. Once the reaction is terminated, water is added to the reaction mixture to hydrolyze the Grignard adduct to the desired tertiary alcohol. The resulting product can then be isolated from the mixture by evaporation of the solvent. The desired product can be purified by recrystallization from a suitable solvent such as benzene.

The described process may be illustrated as follows:

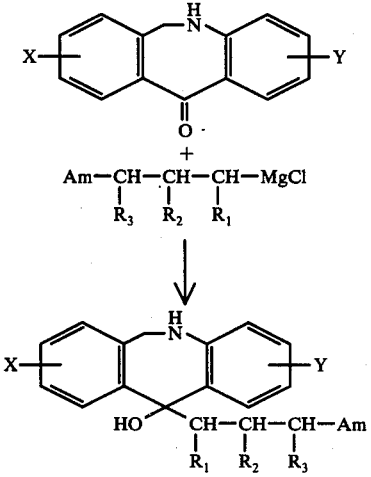

in which all symbols are as previously defined.

The aminoalkyl halide which may be employed in the process is dimethylaminopropyl chloride.

The Grignard reagents may be prepared by conventional methods such as those disclosed in U.S. Pat. No. 2,996,503 and U.S. Pat. No. 3,381,000.

The compounds which may be prepared are:

11-(3-dimethylaminopropyl)-5,6-dihydromorphanthridin-11-ol and
2-chloro-11-(3-dimethylaminopropyl)-5,6-dihydromorphanthridin-11-ol.

The compound in which Z is

may be conveniently prepared by oxidation of the corresponding saturated compound with active manganese dioxide in benzene under reflux conditions.

The process may be illustrated as follows:

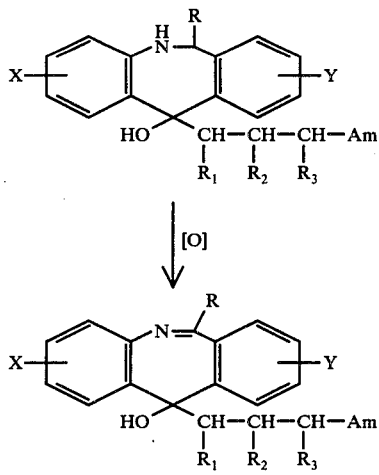

in which X, Y, R, $R_1$, $R_2$, and $R_3$ are hydrogen and Am is

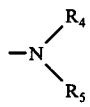

wherein $R_4$ and $R_5$ are methyl and do not interfere with or partake in the reaction.

The compound which can be prepared by the described process is 11-(3-dimethylaminopropyl)-morphanthridin-11-ol.

The compounds of the invention form pharmaceutically acceptable acid addition salts with organic and inorganic acids such as hydrochloric acid, hydrobromic acid, sulfuric acid, acetic acid, maleic acid, succinic acid and glutamic acid. The compounds also form lower alkyl quaternary ammonium salts with reagents such as methyl chloride, ethyl bromide and diethyl sulfate.

The compounds of the present invention are unique in pharmacologic activity. They are highly potent and relatively non-toxic antidepressant agents which appear to possess no undesirable side effects such as anticholinergic activity. In the standard antidepressant test, the compounds 11-(3-dimethyl-aminopropyl-morphanthridin-11-ol and 2-chloro-11-(3-dimethyl-aminopropyl)-5,6-dihydromorphanthridin-11-ol in intraperitoneal doses of 5 to 30 mg/kg antagonize reserpine-induced depression in mice. As antidepressants the compounds appear to be at least ten times more potent than that of imipramine, a well-known antidepressant. In addition, the compounds were found in standard animal tests to have an oral $LD_{50}$ of approximately 130 and 175 mg/kg respectively, which is substantially greater than that of imipramine. Surprisingly the compounds were found to possess no significant anticholinergic activity.

When intended for use as pharmaceutical compositions, the compounds are preferably utilized in the form of acid addition salts. However, the free base form of the compound may be used. The active ingredient is usually combined with conventional pharmaceutical additives such as diluents, flavoring agents and the like. Convenient dosage forms for the compounds are tablets, capsules or liquids for oral or parenteral administration.

In clinical practice, the daily dosage of the active ingredient may range from 5 mg. to 50 mg. or more. The exact amount to be administered will, of course, vary with the patient's size and the severity of his depression.

A typical tablet can have the following composition:

| | |
|---|---|
| 11-(3-dimethylaminopropyl)morphanthridin-11-ol | 10 mg. |
| Lactose U.S.P. | 136.5 mg. |
| Corn Starch U.S.P. | 20.0 mg. |
| Corn Starch (as 10% starch paste) | 3.4 mg. |
| Magnesium Stearate | 1.3 mg. |

Suitable size tablets can be prepared using a 5/16 inch diameter standard convave punch.

Capsules may be prepared by filling No. 3 hard gelatin capsules with the following ingredients, thoroughly mixed:

| | |
|---|---|
| 2-chloro-11-(3-dimethylaminopropyl)-5,6-dihydromorphanthridin-11-ol | 10 mg. |
| Lactose U.S.P. | 195 mg. |
| Starch U.S.P. | 16 mg. |
| Talc U.S.P. | 8 mg. |

The compounds may also be employed to prepare the corresponding 11-aminoalkylidenemorphanthridines, which are useful as anti-Parkinson agents and for the treatment of hypertension.

The following examples illustrate the practice of the invention:

EXAMPLE 1

11-(3-Dimethylaminopropyl)-5,6-dihydromorphanthridin-11-ol

A solution of 5,6-dihydromorphanthridin-11-one (20.9 g., 0.1 M) in 200 ml. of tetrahydrofuran is added dropwise to the Grignard reagent prepared from 48.6 g. (0.4 M) of dimethylaminopropyl chloride, 9.73 g. (0.4 M) of magnesium shavings, and 150 ml. of tetrahydrofuran. The mixture is refluxed for two hours, cooled in ice, and 75 ml. of saturated ammonium chloride solution is added dropwise. The solids are filtered and the solvent removed from the filtrate at reduced pressure. The solid residue is dissolved in 400 ml. of hot acetonitrile and cooled to give 11-(3-dimethylaminopropyl)-5,6-dihydromorphanthridin-11-ol, m.p. 179°–182°.

Anal. Calcd. for $C_{19}H_{24}N_2O$: C, 76.99; H, 8.16; N, 9.45. Found: C, 76.82; H, 8.17; N, 9.50.

EXAMPLE 2

2-Chloro-11-(3-dimethylaminopropyl)-5,6-dihydromorphanthridin-11-ol

A solution of 97.5 g. (0.4 M) of 2-chloro-5,6-dihydromorphanthridin-11-one in 800 ml. of tetrahydrofuran is added to the Grignard reagent prepared from 194 g. (1.6 M) of dimethylaminopropyl chloride, 38.9 g. (1.6 M) of magnesium shavings, and 400 ml. of tetrahydrofuran. After refluxing two hours, the mixture is cooled in ice and decomposed with 230 ml. of saturated ammonium chloride solution. The solids are filtered and the solvent removed from the filtrate. The residue is dissolved in 800 ml. of boiling ethanol and 400 ml. of water and 20 g. of charcoal are added. Filtration and cooling give 2-chloro-11-(3-dimethylaminopropyl)-5,6-dihydromorphanthridin-11-ol, m.p. 135°–137°. An analytical sample recrystallized from 9 volumes of 2:1 ethanol-water has a melting point of 137°–138°.

Anal. Calcd. for $C_{19}H_{23}ClN_2O$: C, 68.97; H, 7.01; Cl, 10.72; N, 8.47. Found: C, 68.92; H, 7.06; Cl, 10.71; N, 8.41.

EXAMPLE 3

11-(3-Dimethylaminopropyl)morphanthridin-11-ol

A mixture of 9.0 g. (0.03 M) of 11-(3-dimethylaminopropyl)-5,6-dihydromorphanthridin-11-ol and 45 g. of active $MnO_2$ is refluxed in benzene for 5 hours. The solids are filtered and rinsed well with benzene. The filtrates are concentrated and the residue is chromatographed on silica. Elution with toluene-methanol (4:1) gives 11-(3-dimethylaminopropyl)morphanthridin-11-ol which, on two recrystallizations from hexane, has a melting point of 95°–102°.

Anal. Calcd. for $C_{19}H_{22}N_2O$: C, 77.51; H, 7.53; N, 9.52. Found: C, 77.37; H, 7.59; N, 9.51.

I claim:

1. A pharmaceutical composition which is intended for use as an antidepressant which comprises an antidepressive amount of a compound of the formula

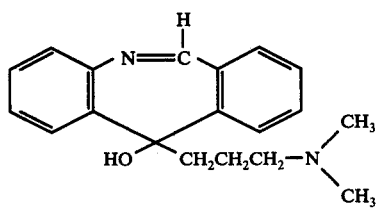

or a pharmaceutically acceptable acid addition salt thereof in combination with a major proportion of a pharmaceutical diluent.

2. The composition of claim 1 wherein the compound is 11-(3-dimethylaminopropyl)morphanthridin-11-ol.

3. A method of effecting antidepressant activity in a depressed animal which comprises administering to said animal a safe and antidepressant effective amount of a pharmaceutical composition of claim 1.

4. A method of effecting antidepressant activity in a depressed animal which comprises administering to said animal a safe and antidepressant effective amount of a pharmaceutical composition of claim 2.

* * * * *